United States Patent
Brockman et al.

(10) Patent No.: US 9,884,035 B2
(45) Date of Patent: Feb. 6, 2018

(54) IMPROVING THE LEVEL OF HYDRATION IN A CAT

(71) Applicant: Hill's Pet Nutrition, Inc., Topeka, KS (US)

(72) Inventors: Jeffrey Brockman, Lawrence, KS (US); Dennis Jewell, Lawrence, KS (US)

(73) Assignee: Hill's Pet Nutrition, Inc., Topeka, KS (US)

(*) Notice: Subject to any disclaimer, the term of this patent is extended or adjusted under 35 U.S.C. 154(b) by 0 days.

(21) Appl. No.: 15/036,226

(22) PCT Filed: Nov. 12, 2013

(86) PCT No.: PCT/US2013/069659
§ 371 (c)(1),
(2) Date: May 12, 2016

(87) PCT Pub. No.: WO2015/072972
PCT Pub. Date: May 21, 2015

(65) Prior Publication Data
US 2016/0296486 A1    Oct. 13, 2016

(51) Int. Cl.
| | | |
|---|---|---|
| A61K 31/20 | (2006.01) | |
| A23D 9/013 | (2006.01) | |
| A23D 9/00 | (2006.01) | |
| A61K 31/202 | (2006.01) | |
| C12Q 1/68 | (2006.01) | |
| A23K 20/158 | (2016.01) | |
| A23K 50/40 | (2016.01) | |
| A61K 9/00 | (2006.01) | |

(52) U.S. Cl.
CPC .......... *A61K 31/202* (2013.01); *A23K 20/158* (2016.05); *A23K 50/40* (2016.05); *A61K 9/0056* (2013.01); *C12Q 1/6883* (2013.01); *C12Q 2600/124* (2013.01); *C12Q 2600/156* (2013.01); *C12Q 2600/158* (2013.01)

(58) Field of Classification Search
CPC .......... A61K 31/20; A23D 9/013; A23D 9/00
USPC .................................. 514/560; 426/531, 601
See application file for complete search history.

(56) References Cited

U.S. PATENT DOCUMENTS

| | | |
|---|---|---|
| 6,946,488 B2 | 9/2005 | Hayek et al. |
| 8,252,742 B2 | 8/2012 | Yamka et al. |
| 2003/0086961 A1 | 5/2003 | Yu et al. |
| 2008/0293621 A1 | 11/2008 | Allen et al. |

FOREIGN PATENT DOCUMENTS

| | | |
|---|---|---|
| AU | 2007290133 | 3/2008 |
| WO | WO 01/082720 | 11/2001 |
| WO | WO 2002/015443 | 7/2002 |

OTHER PUBLICATIONS

Anonymous, 2012, "Feline Genome Project," www.vetmed.ucdavis.edu/catgenetics/feline%20genome%20project/fgp_gr_markers.html.
Bartges et al., 2006. "Nutrition and lower urinary tract disease in cats," Vet Clin. Small Animal Practice 36(6):1361-1376.
Dzanis, 2010, "Cat food's role in urinary tract health now unclear," Petfood Industry, www.petfoodindustry.com/uploadedfiles/petfoodindustry/petfoodindustry201008-dl.pdf.
International Search Report and Written Opinion in International Application No. PCT/US2013/069659, dated Jul. 31, 2014.
Markwell et al., 1998, "The effect of diet on lower urinary tract diseases in cats," J. Nutrition 128:2753S-2757S.
Osborne et al., 1989, "Relationship of nutritional factors to the cause, dissolution, and prevention of feline uroliths and urethral plugs," Veterinary Clinics of North America: Small Animal Practice 19(3):561-581.
Xu et al., 2009, "Effects of dietary sodium chloride on health parameters in mature cats," J. Feline Medicine and Surgery 11(6):435-441.
Plantinga et al., 2005, "Retrospective study of the survival of cats with acquired chronic renal insufficiency offered different commercial diets," Veterinary Record 157:185-187.

*Primary Examiner* — Raymond J Henley, III

(57) ABSTRACT

Methods and compositions for hydrating cats. Cats fed diets containing certain amounts and ratios of arachidonic acid and eicosapentaenoic acid will be sufficiently hydrated and at reduced risk for development of urinary stones, feline idiopathic cystitis, or FLUTD.

13 Claims, 5 Drawing Sheets

IMPROVING THE LEVEL OF HYDRATION IN A CAT

CROSS REFERENCE TO RELATED APPLICATIONS

This application is a United States National Stage Application under 35 U.S.C. 371 of International Application PC/US2013/069659, filed Nov. 12, 2013, the disclosure of which is incorporated herein by reference.

BACKGROUND

The domestic cat (*Felis domesticus*) lives successfully in desert conditions and is adapted to retain water by producing urine which is very concentrated compared to most other mammals. Producing highly concentrated urine, however, can have deleterious effects, such as enhancing development of urinary stones and other less well defined urinary tract conditions such feline idiopathic cystitis. A feline urinary tract condition due to poor hydration is sometimes referred to as Feline Lower Urinary Tract Disease (FLUTD). FLUTD can be a life-threatening condition for cats. In particular, a problem that cat owners face with FLUTD is that the disease is life-threatening to the cat by the time the symptoms are noticeable to the owner. Crystals can precipitate in the cat's urinary tract as stones and Obstruct it. Types of stones include struvite, calcium oxalate, urate, cystine, calcium phosphate, and silicate. Struvite and calcium oxalate stones are by far the most common in cats. If left untreated, a "block" cat will die, as the urine backs up and damages the kidneys, and toxins accumulate in the blood.

If the cat can be induced to drink more, this can dilute the urine and thereby ameliorate feline urinary conditions resulting from low hydration. This dilution acts at two levels: first, by reducing the electrolyte concentration in the urine (assuming the cat is not drinking more simply to compensate for higher dietary salt), and then by increasing micturition frequency and therefore reducing the amount of time spent by the urine in the bladder. Cats generally drink only about 30 milliliters of water per kilo of body weight per day, and it is difficult to increase spontaneous drinking Providing moist food helps to increase water intake in an animal that does not drink very much, but it is not sufficient, either because there is still not enough water ingested or because it does not sufficiently increase diuresis. In addition, cats exhibiting a urological syndrome are often obese or carry excess weight. Thus, when it is desired to treat urinary disorders, and in particular FLUID, providing a moist food may be preferable, but it is not sufficient, i.e., the food does not provide sufficient hydration, may not be accepted by the cat, or even may induce an additional excess weight and/or obesity if the amount distributed is poorly controlled.

Certain cat foods which contain certain omega-3 polyunsaturated fatty acids such as docosahexaenoic acid ("DHA") and eicosapentaenoic acid ("EPA") are known, e.g., as disclosed in U.S. Pat. No. 8,252,742. Certain cat foods are also known to contain both omega-3 and omega-6 polyunsaturated in particular amounts and ratios such as disclosed in U.S. Pat. No. 6,946,488. However, there is no disclosure in the prior art of any effect of such fatty acids in the diet on hydration.

Therefore, there exists today a need for methods and compositions to increase hydration in cats, thereby treating, reducing, inhibiting or ameliorating urinary conditions such as FLUID.

BRIEF SUMMARY

It has been surprisingly discovered that controlling the ratio of certain omega-3 and omega-6 polyunsaturated fatty acids in cat food will result in increased hydration of cats, in particular, the ratio of arachidonic acid ("AA") to EPA. We have found that a high AA to EPA ratio increases urine flow as measured by urine specific gravity in both young and mature adult cats without dehydrating the animal. Blood osmolity indicates that the animals have increased hydration, most likely through increased water intake.

Our studies measured the effect of diets having high vs. low ratios of AA:EPA on both urine specific gravity and relative super saturation (RSS). A high RSS means that a stone is more likely to form (more solutes with which to form stones). Urine specific gravity is positively correlated to (RSS). Cats receiving the high AA:EPA foods had lower urine specific gravity and an improved (lowered) RSS, corresponding to a reduced risk of stone formation.

The present invention concerns a method of improving the level of hydration in a cat comprising feeding the cat a food comprising arachidonic acid and eicosapentaenoic acid wherein the ratio of arachidonic acid to eicosapentaenoic acid is 3:1 or greater and the amount of arachidonic acid is 0.05 to 0.5% dry weight.

In another embodiment the present invention concerns method of treating a disease or condition in a cat resulting from low hydration comprising feeding the cat a food containing arachidonic acid and eicosapentaenoic acid wherein the ratio of arachidonic acid to eicosapentaenoic acid is 3:1 or greater and the amount of arachidonic acid is 0.05 to 0.5% dry weight.

In another embodiment the present invention concerns a palatable, nutritionally complete cat food composition comprising arachidonic acid and eicosapentaenoic acid in an amount effective to improve the hydration in a cat, wherein the food composition, together with water, is palatable and nutritionally complete as a sole diet for the cat, and wherein the ratio of arachidonic acid to eicosapentaenoic acid, on a dry weight basis, is 3:1 or greater, and the ratio, on a dry weight basis, of omega-6 fatty acids to omega-3 fatty acids in the composition is 10:1 to less than 20:1.

Further areas of applicability of the present invention will become apparent from the detailed description provided hereinafter. It should be understood that the detailed. description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

Figure 1:
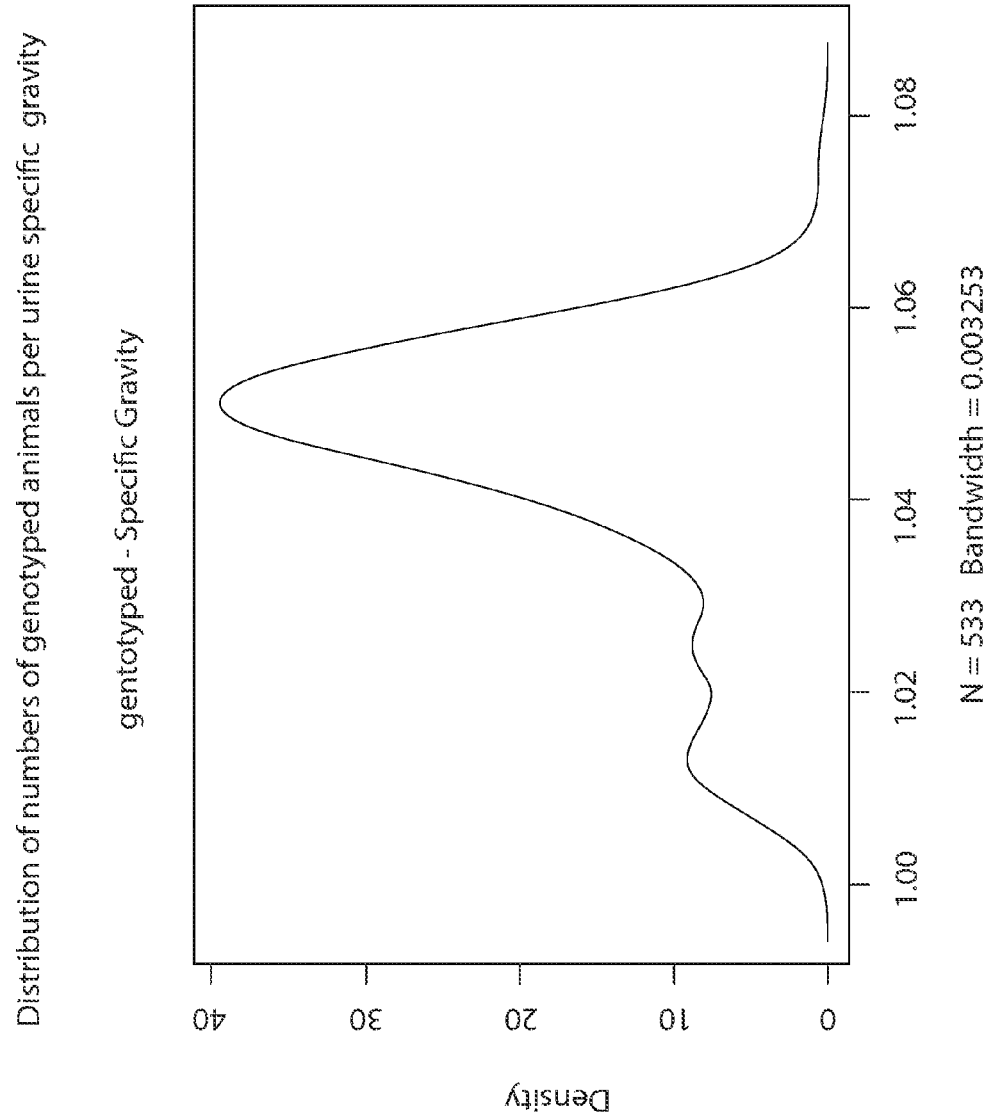
FIG. 1—Distribution of numbers of cats per unit of urine specific gravity (see Example 1). Cats were evaluated for genotypes which were different for high specific gravity (over 1.054 vs below 1.054)
Figure 2:
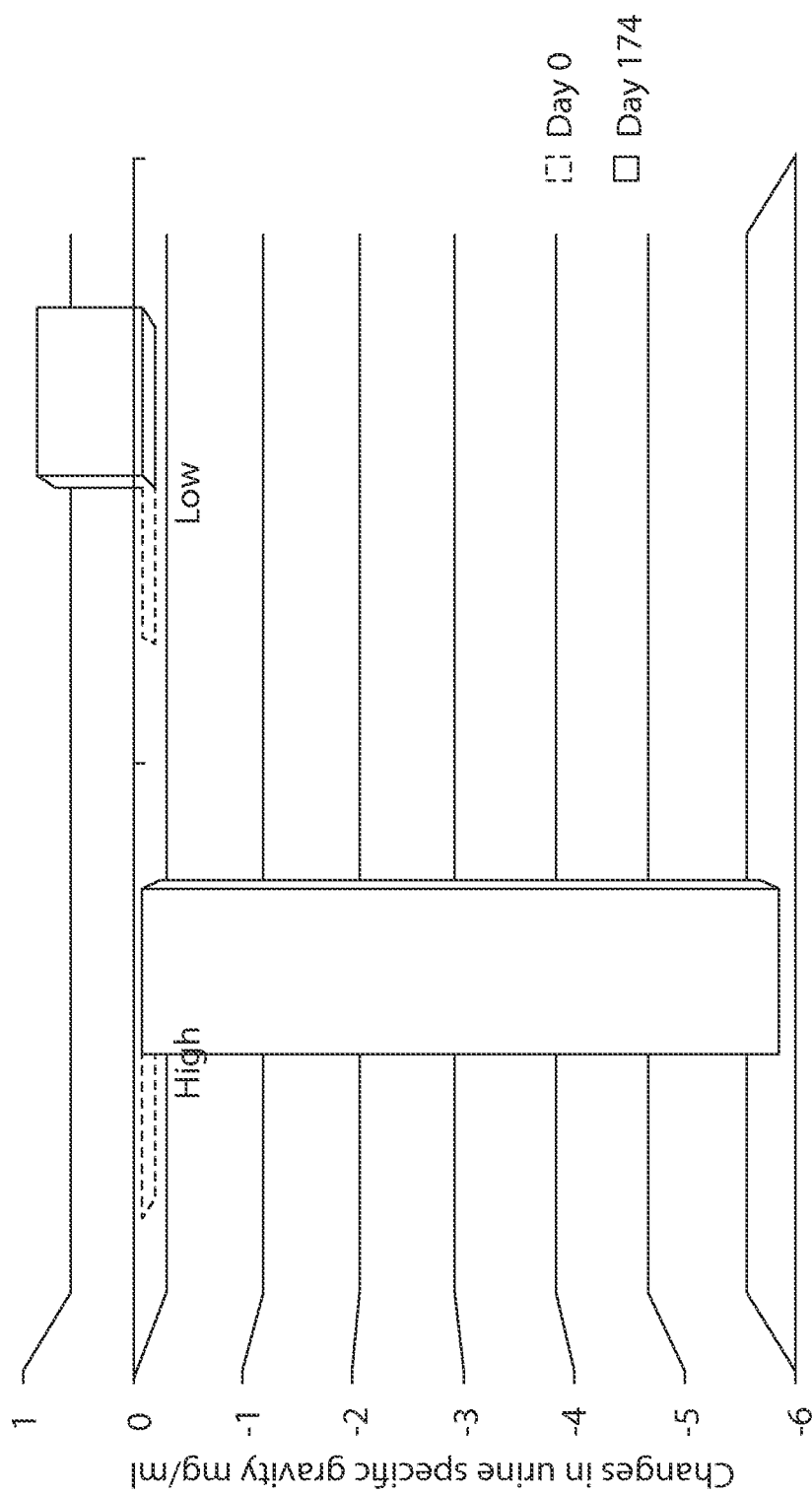
FIG. 2—Bar graph comparing urine specific gravity of mature cats fed a diet having a high ration of AA:EPA (about 3:1) vs. a low ratio of AA:EPA (about 0.5:1) (see Example 2).

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls. Unless otherwise specified, all percentages and amounts expressed herein and elsewhere in the specification should be understood to refer to percentages by weight. All percentages expressed herein are on a weight by dry matter basis unless specifically stated otherwise.

In the context of the invention, the term "treating" or "treatment", as used herein, means reversing, alleviating, mitigating or inhibiting the progress of the disorder or condition to which such term applies, or one or more symptoms of such disorder or condition. As used herein and in the appended claims, the singular forms "a", "an", and "the" include plural reference unless the context clearly dictates otherwise.

Urine specific gravity is a measurement of urine dilution. The higher the specific gravity value the more dense/concentrated the urine is. The normal range for urine specific gravity in a cat is typically between 1.030 and 1.060. A very low specific gravity is indicative of renal failure, whereas a high urine specific gravity means that the urine is more concentrated and therefore it is more likely that stones will precipitate and cause problems.

Urine specific gravity is regulated by a combination of (a) urine production through glomerular filtration into the collecting ducts of the kidney and (b) resorption of water from the collecting duct to go back in to the blood stream. This process is in part regulated by the eicosinoid prostaglandin E2 (PGE2). PGE2 binds to prostaglandin E receptors on the kidney tubular cell and through activation of second messengers, regulates the water and sodium channels that regulate water and sodium balance in the body.

The inventors have discovered a genetic locus containing the prostaglandin E synthase 3 gene, a key enzyme in the pathway that makes PGE2 from AA, using a whole genome association study between the genotypes of cats and their individual urine specific gravity. Furthermore it has been discovered that different ratios of AA (the precursor for PGE2) to EPA in the diet of cats correlate with their urine specific gravities. Thus, it has been discovered that regulating the amount of AA in the diet can lower urine specific gravity in cats. It also has been found that even though the urine is more dilute in cats fed the composition of the invention, their blood osmolality is also decreased indicating that these animals are drinking more water and that their overall water balance is increased, i.e., they are more hydrated.

A high relative super saturation ("RSS") is indicative of a propensity to form urine stones, for both oxalte and struvite stones. It has been discovered that a decline in specific gravity is correlated to a decline in RSS. Therefore, the biological benefit of a more hydrated urine in cats is a reduced risk of stone formation.

In one embodiment, the compositions of the present invention are nutritionally complete cat food compositions. A nutritionally complete composition provides a diet that includes sufficient nutrients for maintenance of normal health of a healthy cat. A nutritionally complete composition is palatable and, together with water, provides the sole source of all of the nutrition necessary for maintenance of normal health in a healthy cat. Nutritionally complete compositions are familiar to one of skill in the art. For example, nutrients and ingredients such as those disclosed herein as well as others suitable for animal feed compositions, and recommended amounts thereof, may be found, for example, in the Official Publication of the Associate of American Feed Control Officials ("AAFCO"), Inc., Nutrient Requirements of Dogs and Cats, 2006. For example, nutritionally complete foods may contain protein, fat, carbohydrate, dietary fiber, amino acids, minerals, vitamins, and other ingredients in amounts known by those of skill in the art.

Protein may be supplied by any of a variety of sources known by those skilled in the art, including plant sources, animal sources, or both. Animal sources include, for example, meat, meat by-products, seafood, dairy, eggs, etc. Meats include, for example, the flesh of poultry, fish, and mammals (e.g., cattle, pigs, sheep, goats, and the like). Meat by-products include, for example, lungs, kidneys, brain, livers, and stomachs and intestines (freed of all or essentially all their contents). The protein can be intact, almost completely hydrolyzed, or partially hydrolyzed. Typical protein amounts in the composition of the invention are at least about 15% (or from about 15% to about 55%, or from about 30% to about 55%, or from about 33% to about 36%).

Fat can be supplied by any of a variety of sources known by those skilled in the art, including meat, meat by-products, fish oil, and plants. Plant fat sources include wheat, flaxseed, rye, barley, rice, sorghum, corn, oats, millet, wheat germ, corn germ, soybeans, peanuts, and cottonseed, as well as oils derived from these and other plant fat sources. The compositions of the invention typically contain at least about 9% (or from about 9% to about 35%, or from about 10% to about 25%, or from about 15% to about 22%) total fat.

AA may be provided from a variety of natural sources. Liver, e.g., chicken liver, is relatively high in AA. Fish oil, on the other hand, is relatively high in EPA, thus not adding fish oil is preferred to avoid high AA:EPA ratios. In addition to AA and EPA, fatty acids which may be included as part of the fat component in the compositions of the present invention include other omega-3 and omega-6 fatty acids such as DHA, alpha-linolenic acid, gamma-linolenic acid, linoleic acid, octadecatetraenoic acid (stearidonic acid), or mixtures thereof. The ratio, on a dry weight basis, of omega-6 to omega-3 fatty acids in the compositions of the invention is typically 10:1 or greater, in another embodiment at least 10:1 to less than 20:1, in another embodiment about 10:1 to 18:1, in another embodiment about 12:1 to 17:1.

Carbohydrate may be supplied by any of a variety of sources known by those skilled in the art, including oat fiber, cellulose, peanut hulls, beet pulp, parboiled rice, corn starch, corn gluten meal, and any combination of those sources. Grains supplying carbohydrate include, but are not limited to, wheat, corn, barley, and rice. Carbohydrate content of foods may be determined by any number of methods known by those of skill in the art. Generally, carbohydrate percentage may be calculated as nitrogen free extract ("NFE"), which may be calculated as follows: NFE=100%−moisture %−protein %−fat %−ash %−crude fiber %.

Dietary fiber refers to components of a plant which are resistant to digestion by an animal's digestive enzymes. Dietary fiber includes soluble and insoluble fibers. Soluble fiber are resistant to digestion and absorption in the small intestine and undergo complete or partial fermentation in the large intestine, e.g., beet pulp, guar gum, chicory root, psyllium, pectin, blueberry, cranberry, squash, apples, oats, beans, citrus, barley, or peas. Insoluble fiber may be supplied by any of a variety of sources, including cellulose, whole wheat products, wheat oat, corn bran, flax seed, grapes, celery, green beans, cauliflower, potato skins, fruit skins, vegetable skins, peanut hulls, and soy fiber. Crude fiber includes indigestible components contained in cell walls and cell contents of plants such as grains, e.g., hulls of grains such as rice, corn, and beans. Typical fiber amounts in the composition of the invention are from about 0 to 10%, or about 1% to about 5%.

Amino acids, including essential amino acids, may be added to the compositions of the present invention as free amino acids, or supplied by any number of sources, e.g., crude protein, to the compositions of the present invention. Essential amino acids are amino acids that cannot be synthesized de novo, or in sufficient quantities by an organism and thus must be supplied in the diet. Essential amino acids vary from species to species, depending upon the organism's metabolism. For example, it is generally understood that the essential amino acids for dogs and cats (and humans) are phenylalanine, leucine, methionine, lysine, isoleucine, threonine, tryptophan, histidine and arginine. In addition, taurine, while technically not an amino acid but a derivative of cysteine, is an essential nutrient for cats.

The compositions of the present invention may also contain one or more minerals and/or trace elements, e.g., calcium, phosphorus, sodium, potassium, magnesium, manganese, copper, zinc, choline, or iron salts, in amounts required to avoid deficiency and maintain health. These amounts are known by those of skill in the art, for example, as provided in the Official Publication of the Associate of American Feed Control Officials, Inc, ("AAFCO"), Nutrient Requirements of Dogs and Cats, 2006. Typical mineral amounts are about 0.1 to about 4% or about 1% to about 2%.

The compositions of the present invention may also include vitamins in amounts required to avoid deficiency and maintain health. These amounts, and methods of measurement are known by those skilled in the art. For example, the Official Publication of the Associate of American Feed Control Officials, Inc ("AAFCO"), Nutrient Requirements of Dogs and Cats, 2006 provides recommended amounts of such ingredients for dogs and cats. As contemplated herein, useful vitamins may include, but are not limited to, vitamin A, vitamin B.sub.1, vitamin B.sub.2, vitamin B.sub.6, vitamin B.sub.12, vitamin C, vitamin D, vitamin F, vitamin H (biotin), vitamin K, folic acid, inositol, niacin, and pantothenic acid. Typical vitamin amounts in the composition of the invention are about from 0 to about 3% or about 1% to about 2%.

The compositions of the present invention may additionally comprise other additives such as palatability enhancers and stabilizers in amounts and combinations familiar to one of skill in the art. Stabilizing substances include, for example, substances that tend to increase the shelf life of the composition. Other examples of other such additive potentially suitable for inclusion in the compositions of the invention include, for example, preservatives, colorants, antioxidants, flavorants, synergists and sequestrants, packaging gases, stabilizers, emulsifiers, thickeners, gelling agents, and humectants. Examples of emulsifiers and/or thickening agents include, for example, gelatin, cellulose ethers, starch, starch esters, starch ethers, and modified starches. The concentration of such additives in the composition typically may be up to about 5% by weight. In some embodiments, the concentration of such additives (particularly where such additives are primarily nutritional balancing agents, such as vitamins and minerals) is from about 0% to about 2.0% by weight. In some embodiments, the concentration of such additives (again, particularly where such additives are primarily nutritional balancing agents) is from about 0% to about 1.0% by weight.

Foods of any consistency or moisture content are contemplated, e.g., the compositions of the present invention may be, for example, a dry, moist or semi-moist animal food composition. In some embodiments, the moisture content is from about 3% to about 90% of the total weight of the composition. "Semi-moist" refers to a food composition containing from about 25 to about 35% moisture. "Moist" food refers to a food composition that has a moisture content of about 60 to 90% or greater. "Dry" food refers to a food composition with about 3 to about 11% moisture content and is often manufactured in the form of small bits or kibbles.

In preparing a composition of the present invention in wet or canned form, any ingredient (e.g., AA, EPA) generally may, for example, be incorporated into the composition during the processing of the formulation, such as during and/or after mixing of other components of the composition. Distribution of these components into the composition can be accomplished by conventional means. In one embodiment, ground animal and poultry proteinaceous tissues are mixed with the other ingredients, including fish oils, cereal grains, other nutritionally balancing ingredients, special-purpose additives (e.g., vitamin and mineral mixtures, inorganic salts, cellulose and beet pulp, bulking agents, and the like); and water that is sufficient for processing is also added. These ingredients preferably are mixed in a vessel suitable for heating while blending the components. Heating of the mixture may be effected using any suitable manner, such as, for example, by direct steam injection or by using a vessel fitted with a heat exchanger. Following the addition of the last ingredient, the mixture is heated to a temperature range of from about 50° F. (10° C.) to about 212° F. (100° C.). In some embodiments, the mixture is heated to a temperature range of from about 70° F. (21° C.) to about 140° F. (60° C.). Temperatures outside these ranges are generally acceptable, but may be commercially impractical without use of other processing aids. When heated to the appropriate temperature, the material will typically be in the form of a thick liquid. The thick liquid is filled into cans. A lid is applied, and the container is hermetically sealed. The sealed can is then placed into conventional equipment designed to sterilize the contents. This is usually accomplished by heating to temperatures of greater than about 230° F. (110° C.) for an appropriate time, which is dependent on, for example, the temperature used and the composition.

Cat food compositions can alternatively be prepared in a dry form using conventional processes. Typically, dry ingredients, including, for example, animal protein, plant protein, grains, etc., are ground and mixed together. Moist or liquid ingredients, including fats, oils, animal protein, water, etc., are then added to and mixed with the dry mix. The mixture is then processed into kibbles or similar dry pieces. Kibble is often formed using an extrusion process in which the mixture of dry and wet ingredients is subjected to mechanical work at a high pressure and temperature, and forced through small openings and cut off into kibble by a rotating knife. The wet kibble is then dried and optionally coated with one or more topical coatings which may include, for example, flavors, fats, oils, powders, and the like. Kibble also can be made from the dough using a baking process, rather than extrusion, wherein the dough is placed into a mold before dry-heat processing.

In the methods of the invention for hydrating cats or for treating a disease or condition in cats, the food administered can be a nutritionally complete cat food or the necessary amounts and ratios of AA and EPA can be administered separately, e.g., as separate ingredient or as part of a separate ingredient, typically as a supplement, so that the total diet consumed meets the amounts and ratios of AA and EPA necessary to result in the beneficial effects of the invention. In the method of the invention of treating a disease or condition in a cat said disease or condition can be, for example, development of urinary stones, feline idiopathic cystitis, or FLUTD.

The invention thus provides in one embodiment, a method of improving the level of hydration in a cat comprising providing the cat with a diet comprising an effective amount of arachidonic acid, wherein the diet comprises a greater amount of arachidonic acid than eicosapentaenoic acid (Method 1). For example, the invention provides 1.1. Method 1 wherein the diet consists of water and a cat food composition which is palatable and nutritionally complete for a cat, the cat food composition comprising arachidonic acid and eicosapentaenoic acid, wherein the ratio of arachidonic acid to eicosapentaenoic acid is 3:1 or greater, e.g., at least 5:1, e.g., at least 10:1, and the amount of arachidonic acid in the composition is 0.05 to 0.5% dry weight.

1.2. Method 1 wherein the diet comprises an effective amount of a supplement comprising arachidonic acid together with a nutritionally complete cat food.

1.3. Method 1, 1.1, or 1.2 wherein the diet comprises omega-6 and omega-3 fatty acids in a weight ratio, on a dry basis, of 10:1 or greater.

1.4. Method 1.3 wherein the ratio, on a dry basis, of omega-6 fatty acids to omega-3 fatty acids in the composition is between 10:1 and 20:1, e.g., 12:1 to 18:1.

1.5. Any of the foregoing methods wherein the cat is an adult cat.

1.6. Any of the foregoing methods wherein the cat is a male cat.

1.7. Any of the foregoing methods which is a method of treating a disease or condition cat resulting from low hydration, wherein the cat is in need of such treatment.

1.8. Method 1.7 wherein the disease or condition is selected from development of urinary stones (including bladder stones or kidney stones), feline idiopathic cystitis, and FLUTD.

1.9. Method 1.7 or 1.8 wherein the cat has been identified being at elevated risk of developing a disease or condition resulting from tow hydration, e.g., a disease or condition selected from development of urinary stones (including bladder stones or kidney stones), feline idiopathic cystitis, and FLUTD, wherein the risk is assessed by (a) measuring the cat's urine specific gravity, and a cat having a urine specific gravity of at least 1.05, e.g. greater than 1.06, e.g. greater than 1.07, is considered to be at elevated risk, and/or (b) wherein the cat expresses a SNP or a mutation in the PTGES3 gene associated with elevated risk.

1.10. The preceding method wherein the cat is identified as being at elevated risk based on exhibiting of one or more single nucleotide polymorphisms (SNPs) selected from chrB4.101464677, chrB4.101341304 and chrB4.101438741.

1.11. Any of the foregoing methods wherein the cat's initial urine specific gravity is greater than 1.055, e.g., greater than 1.06.

1.12. Any of the foregoing methods wherein the cat's urine specific gravity after one month of practice of the method e.g., after three months, e.g., after six months, is reduced relative to the cat's initial urine specific gravity, e.g., to less than 1.055.

1.13. Any of the foregoing methods wherein the cat has a mutation in the PTGES3 gene.

1.14. Any of the foregoing methods wherein the cat exhibits one or more single nucleotide polymorphisms (SNIPs) selected from chrB4.101464677, chrB4.101341304 and chrB4.101438741.

1.15. Any of the foregoing methods wherein the cat remains on the diet for at east a month, e.g., at least three months, e.g., at least six months.

1.16. Any of the foregoing methods wherein the improved hydration in the cat is measured as a decrease in urine specific gravity.

1.17. Any of the foregoing methods wherein the improved hydration in the cat is measured as a decrease in blood osmolality.

1.18. Any of the foregoing methods wherein the method causes an increase in the level of prostaglandin E2.

1.19. Any of the foregoing methods wherein the cat receiving the diet in accordance with the method exhibits increased water intake but not increased sodium chloride intake.

1.20. Any of the foregoing methods wherein the cat receiving the diet is at least 2 years old, e.g., at least 5 years old.

1.21. Any of the foregoing methods wherein the cat's diet comprises any of Composition 1, et seq. as set forth below.

In another embodiment, the invention provides a cat food composition comprising arachidonic acid and eicosapentaenoic acid in an amount effective to improve the hydration in a cat, wherein the food, together with water, is palatable and nutritionally complete as a sole diet for the cat, and wherein the ratio of arachidonic acid to eicosapentaenoic acid, on a dry weight basis, is 3:1 or greater, and the ratio, on a dry basis, of omega-6 fatty acids to omega-3 fatty acids in the composition is 10:1 to less than 20:1 (Composition 1). For example, the invention provides 1.1. Composition 1 wherein the amount of arachidonic acid is 0.05 to 0.5% dry weight.

1.2. Composition 1 or 1.1 wherein the composition comprises at least 5% e.g., at least 7%, of poultry liver, e.g., chicken liver, dry weight, and less than 1% fish oil, dry weight.

1.3. Any of the foregoing compositions comprising ingredients substantially as set forth for Diet B of Example 3 below, wherein by "substantially as set forth" is meant that each listed ingredient is present in the composition an amount of ±5%, e.g., ±2% of the amount as set forth, on a dry weight basis.

1.4. Any of the foregoing compositions in the form of a dry food, e.g., a kibble product.

1.5. Composition 1 or 1.1 for use in any of Methods 1, et seq.

In another embodiment, the invention provides the use of arachidonic acid, or an ingredient or composition comprising arachidonic acid, e.g. any of Compositions 1, et seq, for improving the level of hydration in a cat, e.g., for any of Methods 1, et seq.

In another embodiment, the invention provides the use of arachidonic acid, or an ingredient or composition comprising arachidonic acid, in the manufacture of a cat food composition for use in a method according to any of Methods 1, et seq.

The invention is also directed to methods for identifying cats at elevated risk of developing a disease or condition resulting from low hydration, e.g., a disease or condition selected from development of urinary stones (including bladder stones or kidney stones), feline idiopathic cystitis, and FLUTD, e.g., wherein the risk is assessed by (a) measuring the cat's urine specific gravity, and a cat having a urine specific gravity of at least 1.05, e.g. greater than 1.06, e.g. greater than 1.07, is considered to be at elevated risk, and/or (b) wherein the cat expresses a SNP or a mutation in the PTGES3 gene associated with elevated risk.

For example, in one embodiment, the cat is identified as being at elevated risk based on exhibiting of one or more single nucleotide polymorphisms (SNPs) selected from chrB4.101464677, chrB4.101341304 and chrB4.101438741. Whether a cat has one of these SNPs may be measured by conventional genotyping approaches, e.g. selected from (i) hybridization methods utilizing sequence specific oligonucleotide probes (e.g., dynamic allele-specific hybridization, molecular beacons, or SNP microarrays), (ii) enzyme-based techniques such as restriction fragment length polymorphism (RFLP), polymerase chain reaction methods (e.g., tetra-primer ARMS-PCR with specific primers which can allow detection of the SNPs), flap endonuclease which allows detection of single nucleotide mismatches, primer extension techniques (e.g., hybridization of a probe to the bases immediately upstream of the SNP nucleotide followed by a 'mini-sequencing' reaction, in which DNA polymerase extends the hybridized primer by adding a base that is complementary to the SNP nucleotide), 5"-nucleases using forward and reverse PCR primers that will amplify a region that includes the SNP, and oligonucleotide ligation assays, and (iii) post-amplification methods based on physical properties of DNA, such as single strand conformation polymorphism, temperature gradient gel electrophoresis, denaturing high performance liquid chromatography, high-resolution melting of the entire amplicon, use of DNA mismatch-binding proteins, and commercial systems such as SNPlex (Applied Biosystems). In one embodiment, the SNPs are identified using a SNP microarray such as the Illumina Feline SNP60 array described in Example 1.

An embodiment of the invention thus provides a method of identifying a cat as being at elevated risk of developing a disease or condition resulting from low hydration, e.g., a disease or condition selected from development of urinary stones (including bladder stones or kidney stones), feline idiopathic cystitis, and FLUTD, comprising testing whether the cat exhibits one or more single nucleotide polymorphisms (SNPs) selected from chrB4.101464677, chrB4.101341304 and chrB4.101438741, e.g., using any of the methods of SNP detection as set forth above. In a further embodiment, the invention provides a diagnostic kit for identifying a cat as being at elevated risk of developing a disease or condition resulting from low hydration, e.g., a disease or condition selected from development of urinary stones (including bladder stones or kidney stones), feline idiopathic cystitis, and FLUTD, comprising a sequence specific oligonucleotide probe which recognizes one or more single nucleotide polymorphisms (SNPs) selected from chrB4.101464677, chrB4.101341304 and chrB4.101438741, together with instructions for use.

EXAMPLES

Example 1: Genetic Studies

Urine specific gravity values are determined for 533 cats that have been genotyped using the Illumina Feline SNP60 array (full description table 1).

TABLE 1

Description of the Genotyping array used for the whole genome association study for feline urine specific gravity Illumina, Inc.

| | |
|---|---|
| Descriptor File Name | FelineSNP60_11490519_B.csv |
| Assay Format | Infinium HD Ultra |
| Date Manufactured | Jan. 25, 2011 |
| Loci Count | 62897 |

The distribution of animals per given urine specific gravity is plotted in FIG. 1. Taking the deviation from the normal distribution a quantative trait locus QTL analysis is performed. A Manhattan Plot is constructed, each single nucleotide polymorph ("SNP") genotyped is plotted against the significance of its correlation with the phenotype of urine specific gravity. Only one peak of SNPs is observed significantly above a false discovery cutoff of 10 (−6) indicating that this genetic locus is involved in determining the urine specific gravity. These SNPs are located in a locus on cat chromosome B4. The annotation and p values for the 3 most significant SNPS are given in Table 2. The PTGES3 is the most likely candidate gene in this locus base on biological relevance as described above. This gene is flanked by the three SNPS, two upstream of the start of transcription and one downstream of the transcribed sequence. The positions of the SNPS are given relative to PTGES3 start site of transcription in Table 3 and the location of the PTGES3 gene with in the cat genome is describe in Table 4 including the build of the cat genome assembly used for this analysis.

TABLE 2

Most significant SNPs associated with feline urine specific gravity

| CHR | SNP | A1 | P value |
|---|---|---|---|
| B4 | chrB4.101464677 | A | 1.12E−09 |
| B4 | chrB4.101341304 | A | 2.14E−08 |
| B4 | chrB4.101438741 | A | 3.03E−08 |

TABLE 3

The three most significant SNPs associated with urine specific gravity flank the Prostaglandin E synthase gene (PTGES3)

| CHR | SNP | Genomic position based on cat genome assembly catChrV17e | Genomic position relative to start site of transcription for PTGE3 |
|---|---|---|---|
| B4 | chrB4.101464677 | 97258389 | Plus 22832 |
| B4 | chrB4.101341304 | 97143418 | Minus 92076 |
| B4 | chrB4.101438741 | 97236325 | Plus 768 |

TABLE 4

Description of the Prostaglandin E synthase 3 (PTGES3) gene in the cat genome

The December 2008 *Felis catus* draft assembly, catChrV17e
Position: chrB4: 97211010-97235557
Genomic Size: 24548
Strand: —
Gene Symbol: PTGES3

The three SNP sequences and 200 basepairs flanking sequence are presented below, providing the SNP ID number, the specific SNP, and the sequence of the SNP plus a 200 bp flanking sequence

```
chrB4.101464677 [T/C]
                                      (SEQ. ID. NO. 1)
ATTTTAGAAATCTACCACCGTATGGAGGCAAGTGTAGAGGGATTCTTA

GCCGAGGGTAGAAGAACTATTAGGAAATGATAGCAATAGCCTGGTTCA

GGTGG[T/C]TCTCAGTTAAGGCAGTGGCATTAGGAATGAAGCAATGG

GGGGATAAACAGAAAATATTTAGAAAGTAAATATAGTAGGGAATGGCT

ATGAAGAACTGCTGT chrB4.101341304 [A/G]
                                      (SEQ. ID. NO. 2)
ATAAATTAAACTTCTGTCCAAGATGATGAGTGCATGCAAGAAAGCACC

ACTCACAAAAAATGGGATAGGGACACCATAATGGAGTGAGGACCTTT

ACTC[A/G]GGCTGGGAAATCTTCCCACCCTCCAGTCTGGAAGTTTTA

TTTTGGTGAACCCTCTAAAGATACAAGGTACAGGAACACCAGCTTCCA

GCACCATAAAAAT chrB4.101438741 [A/G]
                                      (SEQ. ID. NO. 3)
CAGTGGAGAGTCGAAGTTTGTGGGAATGGGGAGAGAGATGAGGACACT

CCTTGTCTTCAGGCACATCATTAGGGGGAGAAGGTTACCCATCTGTTT

TCA[A/G]CCATTATCTCTTGAACTGCCGCTTTGTCCCTTGAACGTGG

TTGGGCTGTAATGAGGGATAGTAACCAAGAGAATGAAAACAGTACTTA

CTGCCTATTGTA
```

Example 2: A Study in Mature Cats Using Differential Ratios of AA to EPA

In Diet 1 the AA ratio to EPA is 3 to 1, and in Diet 2 the ratio of AA to EPA is 0.5 to 1. Diet 1 contains 20.84% total fat, 0.10% AA (0.48% total fat) and 0.03% EPA (0.14% total fat). The test foods contained approximately 31.5% protein, The high AA ratio fat concentration was 20.8% while the low AA to EPA ratio was 15.7% fat. The ratio of omega 6 fatty acids to omega-3 fatty acids in Diet 1 is 14.4. The animals are maintained on the two diets (27 cats fed the high AA to EPA ratio and 54 cats fed the low AA to EPA ratio). Urine is collected and analyzed for urine specific gravity at day 0 and day 180, data presented in Table 5 (g/ml):

TABLE 5

Urine Specific Gravity Change in Senior Cats

|  | Day 0 | Day 180 |
|---|---|---|
| High | 1.06 | 1.054 |
| Low | 1.06 | 1.061 |

The group of cats on the high AA ratio diet (High) exhibits a significantly reduced urine specific gravity after 180 days. The group of cats on the low AA ratio diet (Low) exhibits no change in their urine specific gravity. In addition to urine specific gravity, blood osmolality is also measured as an indicator of level of hydration, data presented in Table 6 (mM/liter):

TABLE 6

In mature cats a high AA to EPA ratio decreases blood osmolality

|  | Day 0 | Day 180 |
|---|---|---|
| High | 323.2 | 306.3 |
| Low | 314 | 315.7 |

Figure 3:
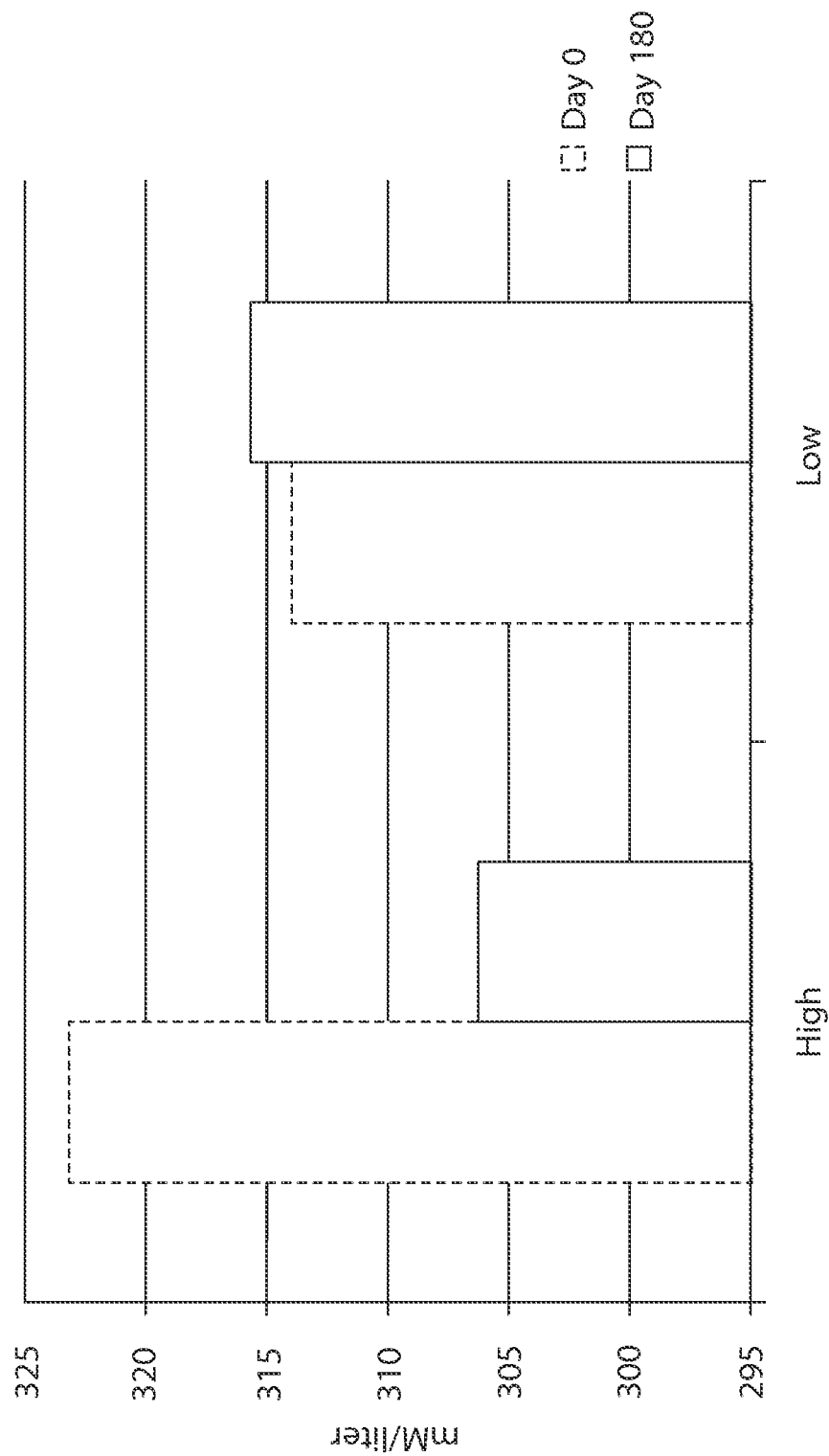
FIG. 3—Bar graph comparing blood osmolality of mature cats fed a diet having a high ration of AA:EPA (about 3:1) vs. a low ratio of AA:EPA (about 0.5:1) (see Example 2).
Figure 4:
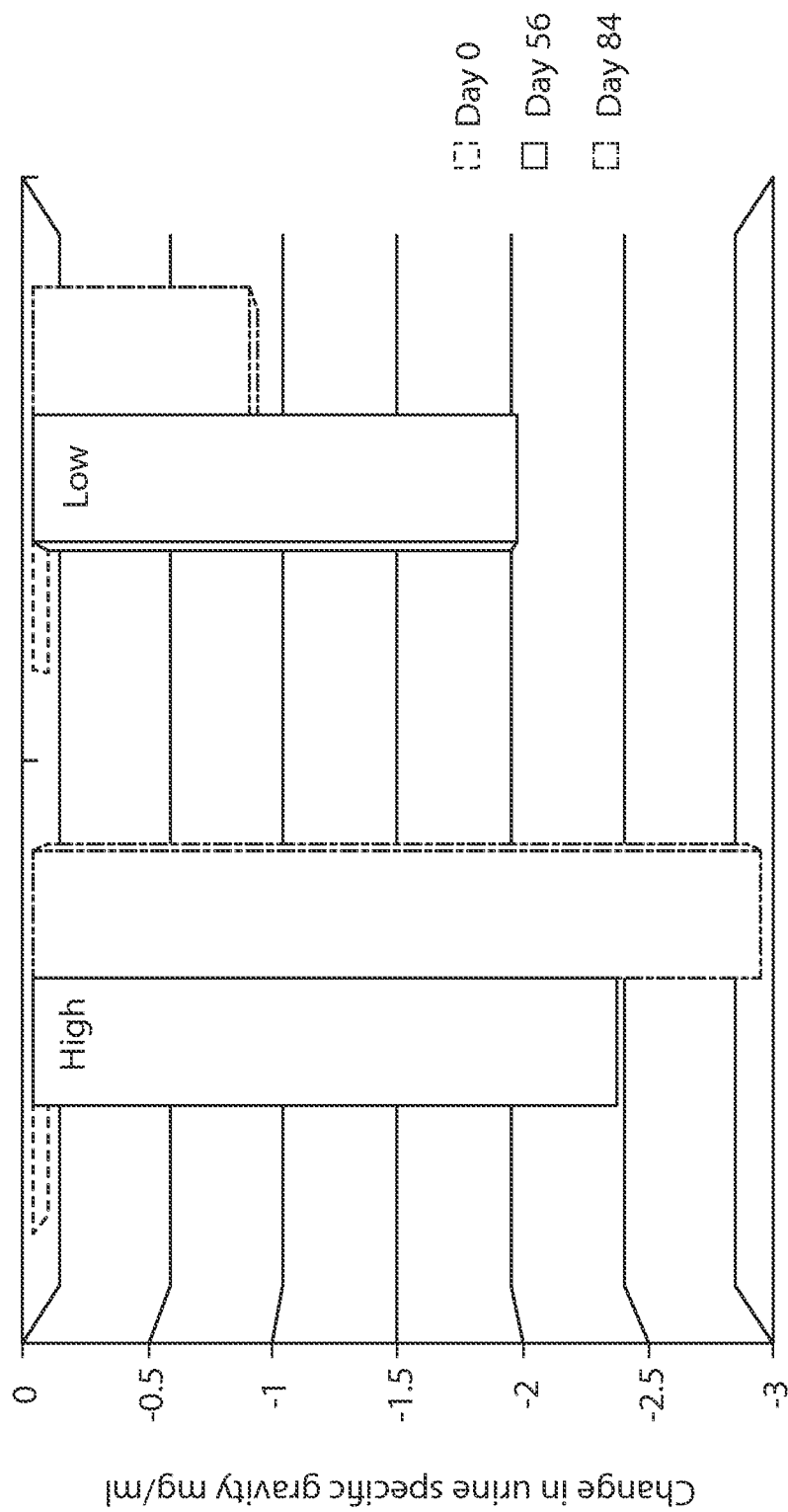
FIG. 4—Bar graph comparing urine specific gravity of young cats fed a diet having a high ratio of AA:EPA (16:1 and 8:1) vs. a low ratio of AA:EPA (0.4:1) (see Example 3).
Figure 5:
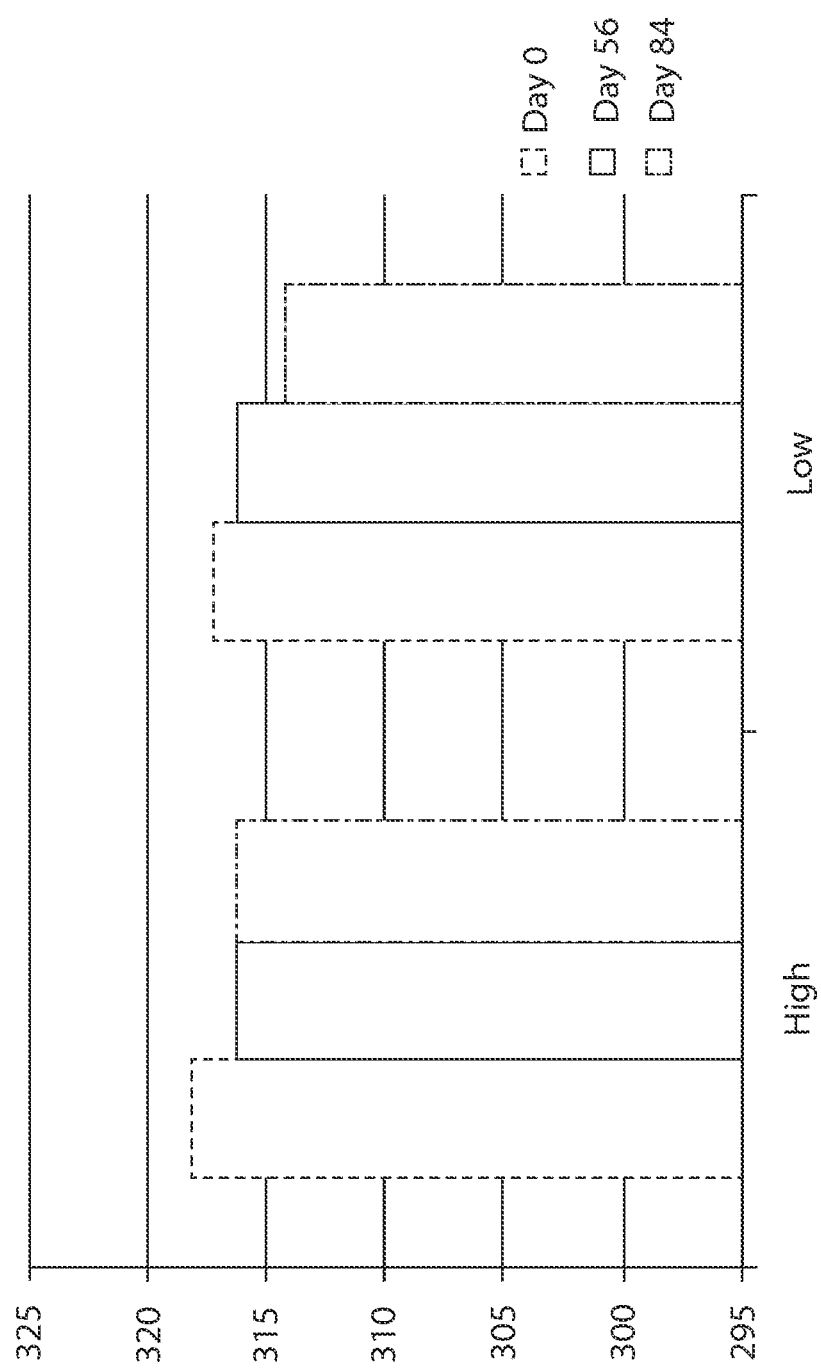
FIG. 5—Bar graph comparing blood osmolality of young cats fed a diet having a high ration of AA:EPA (about 16:1 and 8:1) vs. a low ratio of AA:EPA (0.4:1) (see Example 3).

As with urine specific gravity, there is a significant decrease in blood osmolality in cats fed the high AA diet but no change in the cats fed the low AA to EPA ratio (FIG. 3). This indicates that not only does the high level of AA make the urine more dilute, but that the blood is also more dilute, indicating that the cats are taking in more water and that their overall water balance is increased. In other words, the cats are more hydrated.

Example 3: A Feeding Study in Kittens with Differential Ratios of AA to EPA

In the control diet, the ratio of AA to EPA is 0.4 to 1 in Diet A (the increased AA/EPA diet) the ratio of AA to EPA is >8 to 1, and in Diet B (the further increased AA/EPA diet) the ratio of AA to EPA is >16 to 1. The control diet contains 15.06% total fat, 0.09% AA (0.6% total fat) and 0.23% EPA (1.53% total fat); Diet A contains 14.67% total fat, 0.08% AA (0.55% total fat) and <0.01% EPA (<0.01% total fat); and Diet B contained 16.01% total fat, 0.16% AA (1% total fat) and <0.01% EPA (<0.01% total fat). The ratio of omega-6 fatty acids to omega-3 fatty acids in Diet A is 18.1 and in Diet B is 17.5. The animals are maintained on the three diets. Urine is collected and analyzed for urine specific gravity at day 0, day 28 and day 56. The results are as set forth in Table 3 (g/ml):

TABLE 7

Urine Specific Gravity Change in Kittens

|  | Day 0 | Day 28 | Day 56 |
|---|---|---|---|
| Control | 1.057 | 1.057 | 1.057 |
| Diet A | 1.057 | 1.054 | 1.053 |
| Diet B | 1.057 | 1.054 | 1.054 |

The group of kittens on Diets A and B, the high AA ratio diet had a significantly reduced urine specific gravity after 28 days. The group of kittens on the control diet saw no change in their urine specific gravity.

Unlike the older cats, the kittens did not show significant differences in blood osmolality. See Table 8 (values in mM/liter):

TABLE 8

In kittens, a high AA to EPA ratio does not influence blood osmolality

|  | Day 0 | Day 28 | Day 56 |
|---|---|---|---|
| Control | 317 | 316 | 314 |
| Diet A | 317 | 315 | 316 |
| Diet B | 318 | 316 | 316 |

These data suggest that the ability to maintain normal osmolality values may be better in younger animals, regardless of diet, which may help explain why stones are more prevalent as the animals get older. This suggests that diet may have a greater influence on stone formation in older animals.

The formulations for Control diet, Diet A and Diet B are as follows:

TABLE 9

| Description | % | % | % |
|---|---|---|---|
| Rice | 40 | 40 | 40 |
| Chicken Protein and amino acids | 20 | 20 | 16 |
| Plant Protein | 25 | 25 | 21 |
| Animal Fat | 8 | 10 | 9 |
| Chicken, liver |  |  | 7.50 |
| Minerals | 3 | 3 | 3 |
| Vitamins | 1 | 1 | 1 |
| Fish oil | 1.40 |  |  |
| Palatability Enhancer | 1 | 1 | 1 |
| Water, preservatives and processing | 1 | 1 | 1 |
| Arachidonic (AA) % analyzed | 0.11 | 0.09 | 0.16 |
| EPA % analyzed | 0.22 | <0.01 | <0.01 |

Example 4

Correlation Calcium Oxalate RSS with AA and EPA

The CORR Procedure 2 with variables: AA, EPA
1 variable: calcium oxalate RSS

| | Pearson Correlation Coefficients<br>Prob > \|r\| under H0: Rho = 0<br>Number of observations |
|---|---|
| AA | −0.44188<br><.0001<br>97 |

The GLM Procedure

Dependent variable: Calcium oxalate RSS
1 with variables: ratio
1 variable: calcium oxalate RSS

| | Pearson Correlation Coefficients<br>Prob > \|r\| under H0: Rho = 0<br>Number of observations |
|---|---|
| Ratio | −0.38885<br><.0001<br>96 |

There is a significant relationship, in that increased AA in the blood is associated with a decreased RSS while an increased EPA concentration is associated with an increased RSS.

We claim:

1. A method of improving the level of hydration in a cat comprising providing the cat with a diet comprising an effective amount of arachidonic acid and eicosapentaenoic acid, wherein the diet comprises a greater amount of arachidonic acid than eicosapentaenoic acid.

2. The method of claim 1, wherein the diet comprises water and a cat food composition which is palatable and nutritionally complete for a cat, the cat food composition comprising arachidonic acid and eicosapentaenoic acid, wherein the ratio of arachidonic acid to eicosapentaenoic acid is 3:1 or greater, and the amount of arachidonic acid in the composition is 0.05 to 0.5% dry weight.

3. The method of claim 1, wherein the diet further comprises an effective amount of a supplement comprising arachidonic acid together with a nutritionally complete cat food.

4. The method of claim 1, wherein the diet further comprises omega-6 and omega-3 fatty acids in a weight ratio, on a dry basis, of 10:1 or greater.

5. The method of claim 1, which is a method of treating a disease or condition in a cat resulting from low hydration, wherein the cat is in need of such treatment.

6. The method of claim 5, wherein the disease or condition is selected from development of urinary stones, feline idiopathic cystitis, and FLUTD.

7. The method of claim 5, wherein the cat has been identified as being at elevated risk of developing a disease or condition resulting from low hydration, wherein the risk is assessed by (a) measuring the cat's urine specific gravity, and/or (b) exhibition of a SNP or a mutation in the PTGES3 gene associated with elevated risk.

8. The method of claim 7 wherein the cat is identified as being at elevated risk based on exhibiting of one or more single nucleotide polymorphisms (SNPs) selected from chrB4.101464677, chrB4.101341304 and chrB4.101438741.

9. The method of claim 1, wherein the cat's urine specific gravity after one month of practice of the method is reduced relative to the cat's initial urine specific gravity.

10. The method of claim 1, wherein the cat remains on the diet for at least a month.

11. A cat food composition comprising arachidonic acid, eicosapentaenoic acid, omega-6 fatty acids, and omega-3 fatty acids in an amount effective to improve the hydration in a cat, wherein the food, together with water, is palatable and nutritionally complete as a sole diet for the cat, and wherein the ratio of arachidonic acid to eicosapentaenoic acid, on a dry weight basis, is 3:1 or greater, and the ratio of omega-6 fatty acids to omega-3 fatty acids, on a dry basis, in the composition is 10:1 to less than 20:1.

12. The composition of claim 11 wherein the amount of arachidonic acid is 0.05 to 0.5% dry weight.

13. The composition of claim 11, wherein the composition further comprises at least 5% of poultry liver, dry weight, and less than 1% fish oil, dry weight.

* * * * *

SEQUENCE LISTING

<160> NUMBER OF SEQ ID NOS: 3

<210> SEQ ID NO 1
<211> LENGTH: 201
<212> TYPE: DNA
<213> ORGANISM: Felis catus

<400> SEQUENCE: 1

```
attttagaaa tctaccaccg tatggaggca agtgtagagg gattcttagc cgagggtaga      60
agaactatta ggaaatgata gcaatagcct gttcaggtgg ytctcagtta aggcagtggc     120
attaggaatg aagcaatggg gggataaaca gaaaatattt agaaagtaaa tatagtaggg     180
aatggctatg aagaagtctg t                                                201
```

<210> SEQ ID NO 2
<211> LENGTH: 201
<212> TYPE: DNA
<213> ORGANISM: Felis catus

<400> SEQUENCE: 2

```
ataaattaaa cttctgtcca agatgatgag tgcatgcaag aaagcaccac tcacaaaaaa      60
atgggatagg gacaccataa tggagtgagg acctttactc rggctgggaa atctttccac     120
cctccagtct ggaagtttta ttttggtgaa ccctctaaag atacaaggta caggaacacc     180
agcttccagc accataaaaa t                                                201
```

```
<210> SEQ ID NO 3
<211> LENGTH: 201
<212> TYPE: DNA
<213> ORGANISM: Felis catus

<400> SEQUENCE: 3
cagtggagag tcgaagtttg tgggaatggg gagatgagat gaggacactc cttgtcttca        60
ggcacatcat taggggggaga aggttaccca tctgttttca rccattatct cttgaactgc      120
cgctttgtcc cttgaacgtg gttgggctgt aatgagggat agtaaccaag agaatgaaaa      180
cagtacttac tgcctattgt a                                                  201
```